US010085850B2

(12) United States Patent
Smith

(10) Patent No.: US 10,085,850 B2
(45) Date of Patent: Oct. 2, 2018

(54) COMPOSITE BONE GRAFTS AND METHODS FOR PRODUCING THE SAME

(71) Applicant: DCI Donor Services, Inc., Nashville, TN (US)

(72) Inventor: David Ayres Bowden Smith, Golden, CO (US)

(73) Assignee: David Ayres Bowden Smith, Golden, CO (US)

( * ) Notice: Subject to any disclaimer, the term of this patent is extended or adjusted under 35 U.S.C. 154(b) by 16 days.

(21) Appl. No.: 15/512,007

(22) PCT Filed: Sep. 16, 2015

(86) PCT No.: PCT/US2015/050534
§ 371 (c)(1),
(2) Date: Mar. 16, 2017

(87) PCT Pub. No.: WO2016/044495
PCT Pub. Date: Mar. 24, 2016

(65) Prior Publication Data
US 2017/0290672 A1 Oct. 12, 2017

Related U.S. Application Data

(60) Provisional application No. 62/050,912, filed on Sep. 16, 2014.

(51) Int. Cl.
*A61F 2/28* (2006.01)
*A61F 2/44* (2006.01)
*A61F 2/30* (2006.01)
(52) U.S. Cl.
CPC .......... *A61F 2/447* (2013.01); *A61F 2/30771* (2013.01); *A61F 2/446* (2013.01);
(Continued)

(58) Field of Classification Search
CPC ........ A61F 2/446; A61F 2/445; A61F 2/1165; A61F 2/447; A61F 2/1601;
(Continued)

(56) References Cited

U.S. PATENT DOCUMENTS 5,192,327 A * 3/1993 Brantigan ................. A61F 2/44
606/247
6,025,538 A * 2/2000 Yaccarino, III ........... A61F 2/28
128/898

(Continued)

OTHER PUBLICATIONS

Smith GW, Robinson RA. The treatment of certain cervical-spine disorders by anterior removal of the intervertebral disc and interbody fusion. Journal of Bone and Joint Surgery American. Jun. 1958;40-A(3):607-24.

*Primary Examiner* — Alvin Stewart
(74) *Attorney, Agent, or Firm* — Stites & Harbison PLLC; Richard S. Myers, Jr.

(57) ABSTRACT

The present disclosure is directed to composite bone grafts and to methods for providing such grafts for orthopedic and other surgical uses in a subject in need thereof. In some embodiments, the present disclosure provides a method for producing a composite bone graft, the method comprising, for example, the steps of: (i) selecting at least one donor site on at least one subject; (ii) removing at least one piece of bone, comprising cortical bone, from the at least one donor site; (iii) machining the at least one piece of bone to produce at least two bone components, each having a surface comprising at least one of a protuberance and a recess thereon; and (iv) joining the at least two machined bone components to produce a composite bone graft.

33 Claims, 11 Drawing Sheets

(52) U.S. Cl.
CPC ...... *A61F 2/4455* (2013.01); *A61F 2002/305* (2013.01); *A61F 2002/3082* (2013.01); *A61F 2002/3085* (2013.01); *A61F 2002/30199* (2013.01); *A61F 2002/30224* (2013.01); *A61F 2002/30604* (2013.01); *A61F 2002/30904* (2013.01); *A61F 2310/00011* (2013.01); *A61F 2310/00023* (2013.01); *A61F 2310/00359* (2013.01)

(58) Field of Classification Search
CPC ............ A61F 2002/4615; A61F 2/4618; A61F 2002/2839; A61F 2/2846; A61F 2002/30759; A61F 2002/30764; A61F 2002/30766; A61F 2/30771; A61F 2/30747; A61F 2002/30754; A61F 2/30756; A61F 2002/30761; A61F 2/4644; A61F 2/28; A61F 2002/2835; A61F 2002/2842
See application file for complete search history.

(56) References Cited

U.S. PATENT DOCUMENTS

| | | | | |
|---|---|---|---|---|
| 6,159,244 | A * | 12/2000 | Suddaby | A61F 2/4455 606/247 |
| 7,094,257 | B2 * | 8/2006 | Mujwid | A61F 2/447 623/17.15 |
| 7,618,458 | B2 * | 11/2009 | Biedermann | A61F 2/442 623/17.15 |
| 9,414,934 | B2 * | 8/2016 | Cain | A61F 2/442 |
| 9,913,676 | B2 * | 3/2018 | Schlachter | A61B 17/8816 |
| 2005/0107878 | A1 * | 5/2005 | Conchy | A61F 2/44 623/17.11 |
| 2005/0125062 | A1 * | 6/2005 | Biedermann | A61F 2/442 623/17.11 |
| 2006/0212036 | A1 * | 9/2006 | Bianchi | A61F 2/0811 623/13.14 |
| 2006/0241763 | A1 * | 10/2006 | Paul | A61F 2/28 623/17.11 |
| 2008/0103601 | A1 * | 5/2008 | Biro | A61F 2/44 623/17.16 |
| 2008/0103602 | A1 * | 5/2008 | Berry | A61F 2/44 623/17.16 |
| 2010/0049325 | A1 * | 2/2010 | Biedermann | A61F 2/442 623/17.16 |
| 2010/0121453 | A1 * | 5/2010 | Peterman | A61F 2/4455 623/17.11 |
| 2013/0268075 | A1 | 10/2013 | McKay | |
| 2013/0325142 | A1 * | 12/2013 | Hunter | C22C 1/08 623/23.51 |
| 2014/0025168 | A1 * | 1/2014 | Klimek | A61F 2/442 623/17.16 |
| 2014/0121777 | A1 | 5/2014 | Rosen et al. | |
| 2014/0207235 | A1 * | 7/2014 | Drapeau | A61F 2/442 623/17.16 |
| 2016/0106540 | A1 * | 4/2016 | Kuntz | A61L 27/10 623/23.51 |

* cited by examiner

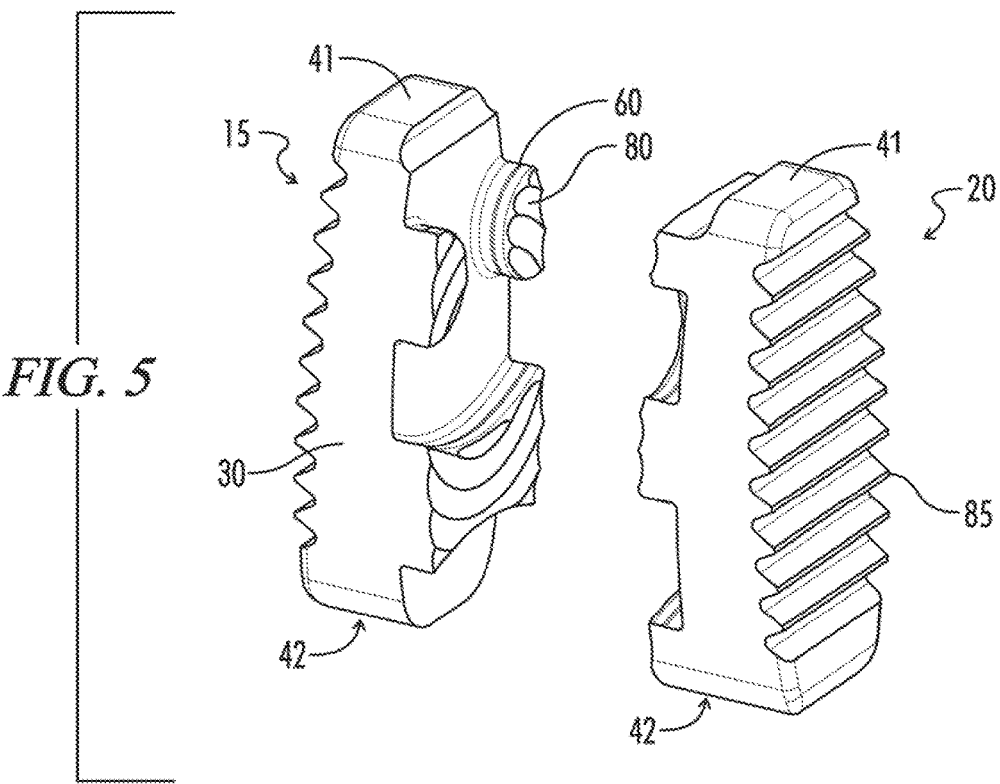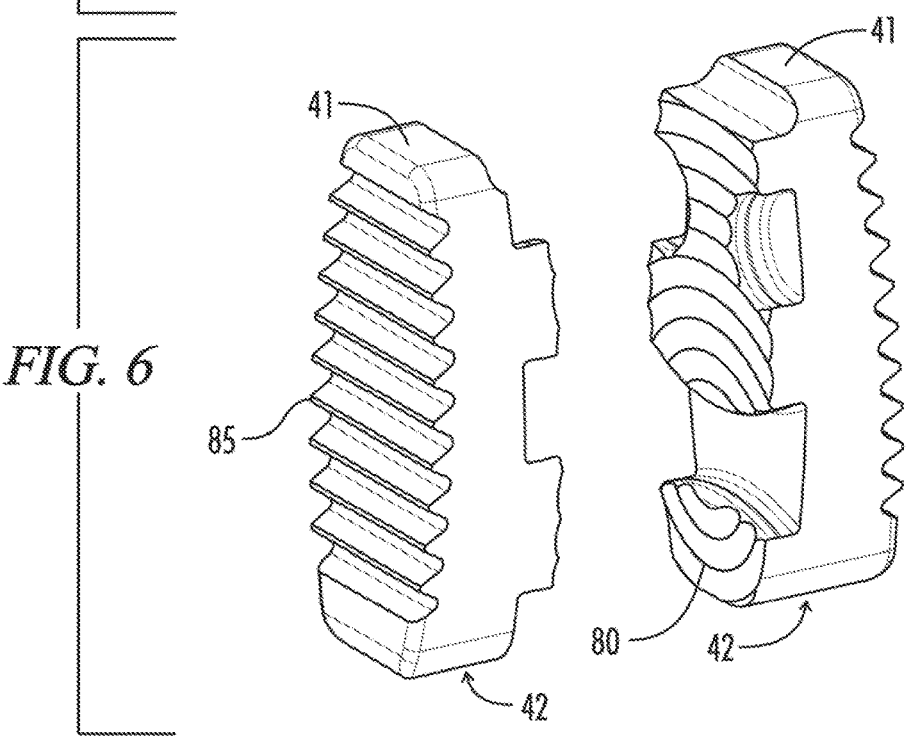

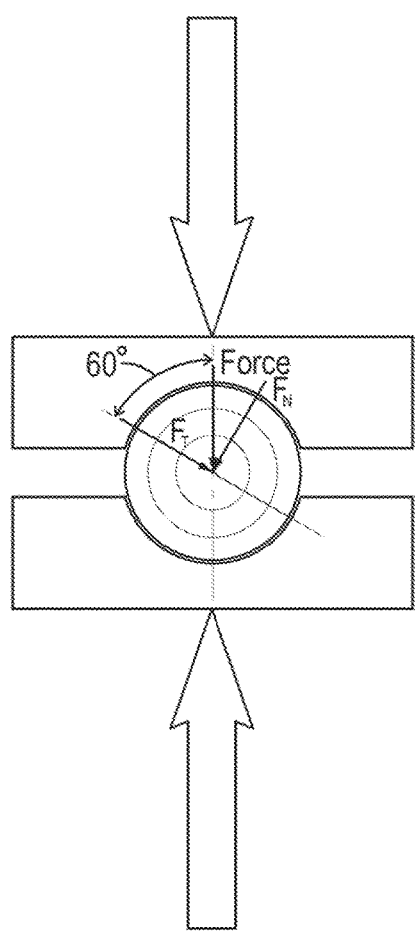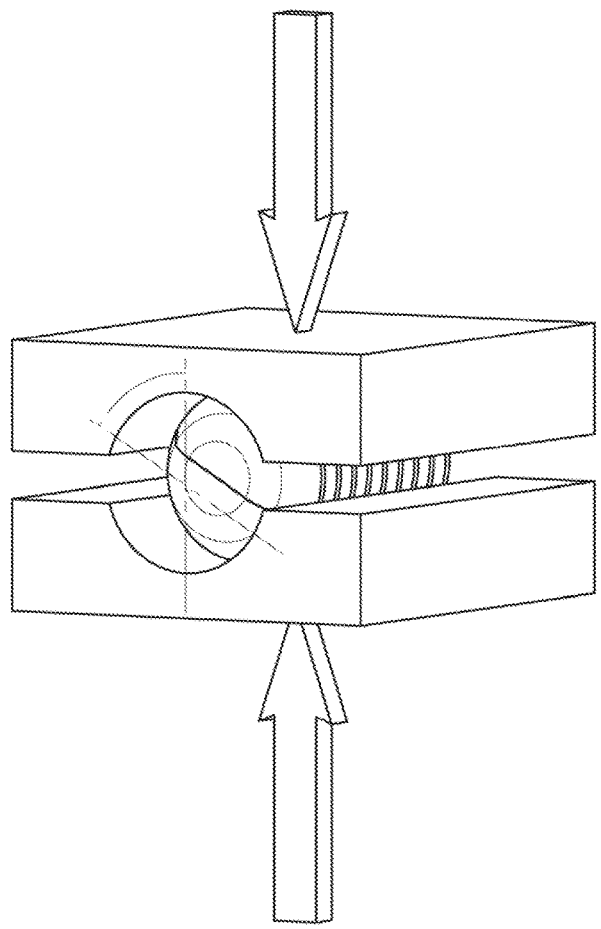
*FIG. 14*  *FIG. 15*

COMPOSITE BONE GRAFTS AND METHODS FOR PRODUCING THE SAME

CROSS REFERENCE TO RELATED APPLICATIONS

This application is a § 371 National State Application of PCT/US2015/050534 filed Sep. 16, 2015 which claims priority to provisional application No. 62/050,912 filed Sep. 16, 2014.

TECHNICAL FIELD

The present disclosure is directed to composite bone grafts and to methods for providing such grafts for orthopedic and other surgical uses in a subject in need thereof. More specifically, the disclosure is directed to bone graft components comprising cortical bone and to methods of manufacture, production, and/or manipulation of the same.

INTRODUCTION

Numerically controlled (NC) machining technology was initially developed in the 1940s and the 1950s. With this technology, a series of positional commands were sent to machining mills to cut metals and later plastics. Three-dimensional location points (X,Y,Z points), cutting speeds, and/or spindle speeds (in revolutions per minute) were sent to the milling machine via punch cards or punched paper tape. The next decades saw the transition from NC machining to computer numerically controlled (CNC) machining, wherein commands were executed by a computer controlling the milling system. The CNC machining mills became increasingly complex, and the ability to manufacture complex parts for the automotive, aerospace, consumer products, and medical products industries flourished. Indeed, CNC technology was applied to more manufacturing methods, such as water-jet cutting, electrical discharge machining (EDM), lathes for turning, and many others. In the late 1990's, tissue banks began to apply CNC machining for the manufacture of cortical bone and cancellous bone allografts.

SUMMARY

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of features.

In some embodiments, the present disclosure provides a method for producing a composite bone graft, the method comprising, for example, the steps of: (i) selecting at least one donor site on at least one subject; (ii) removing at least one piece of bone, comprising conical bone, from the at least one donor site; (iii) machining the at least one piece of bone to produce at least two bone components, each having a surface comprising at least one of a protuberance and a recess thereon; and (iv) joining the at least two machined bone components to produce a composite bone graft. In further embodiments, all or some of the machining of the bone pieces may be completed before removing the pieces of bone from the donor site of the donor bone. In further embodiments, the methods of the present disclosure may additionally comprise any of the steps of (v) machining mating surface features on the at least two bone components, (vi) bonding and/or sealing the at least two machined bone components together, and/or (vii) joining the at least two machined bone components by interlocking and/or interdigitating any of the at least one of a protuberance and a recess of a first bone component with the at least one of a protuberance and a recess of a second bone component and/or (viii) implanting the composite bone graft in a subject. Further, in some embodiments, the composite bone graft comprises at least one of cortical bone, cancellous bone, titanium, carbon fiber, other implantable material, or any combination thereof. The cortical bone and/or cancellous bone may be partially or fully demineralized.

In some embodiments, the present disclosure is directed to a composite bone graft comprising at least two machined component bone pieces that are assembled and/or releasably connected to one another to form the composite graft. In certain embodiments, each of the component bone pieces comprises at least one surface having at least one protuberance and % or at least one recess thereon. And in further embodiments, the protuberance and/or recess of a surface of a first component may be interdigitated with a protuberance and/or recess of a surface of a second component to form a composite graft. As used herein, the term "protuberance" refers to any portion of the bone component (or other material) that projects from and above the lower machined surfaces. The term "recess" is used herein to refer to a region defined by the lower machined surface and the sides (vertical walls) of the protuberance(s). Accordingly, the protuberance of one component can fit into the recess of a mating component.

A known "dovetail" fit between components relies on those components sliding against each other during assembly and creating some degree of residual stress to maintain positioning. With a dovetail fit, the path of the dovetail profile is either cut in a straight line or cut in a circular arc. If one or both components are flexible then the path of the dovetail fit can be either approximately straight or approximately circular. In contrast, embodiments of the present grafts were developed such that they can be pressed together in a direction substantially perpendicular to the mating surfaces of the components, as opposed to parallel to the mating surfaces as would be the case with a dovetail fit. With embodiments of the present grafts, elastic deformation between the two components is created during assembly; the top section of each protuberance will interfere with one another when the components are assembled, and in snapping the components together, elastic deformation between the two components will occur in order for the pieces to come together. After assembly, this elastic deformation will be recovered as the pieces become fully mated and the inner section of one component matches with the outer section of the other, thereby reducing or eliminating residual stress on the construct.

Additionally, a dovetail fit typically relies on simple path taken by the dovetail cutter, i.e., straight or gently curved, whereas embodiments of the present grafts comprise complex paths of the profile of the mating surfaces. The term "complex" is used herein to refer to shapes that include a plurality of curves (i.e., circular, sinusoidal, parabolic, elliptical, splines, and other curve types), the same or different from one another, as well as shapes that include any combination of straight lines and curves.

Furthermore, in some embodiments a press-fit between components is accomplished by including an upper protuberance radius (outer radius) that is greater than a lower radius (inner radius).

In some embodiments, in order to provide additional surface area for bony apposition between the host bone and the allograft bone, the top surfaces of the protuberances are not flat but rather have channels cut in them. The channels in some embodiments have depth of about 0.001, 0.002, 0.003, 0.004, 0.005, 0.006, 0.007, 0.008, 0.009, 0.010, 0.011, 0.012, 0.013, 0.014, 0.015.0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.100, 0.110, 0.120, 0.130, 0.140, 0.150, 0.160, 0.170, 0.180, 0.190, 0.200, 0.210, 0.220, 0.230, 0.240, 0.250, 0.260, 0.270, 0.280, 0.290, 0.300, 0.310, 0.320, 0.330, 0.340, 0.350, 0.360, 0.370, 0.380, 0.390, 0.400, 0.410, 0.420, 0.430, 0.440, 0.450, 0.460, 0.470, 0.480, 0.490, 0.500, 0.550, 0.600, 0.650, 0.700, 0.750, 0.800, 0.850, 0.900, 0.950, 1.000, 1.100, 1.200, 1.300, 1.400, 1.500, 1.600, 1.700, 1.800, 1.900, 2.000, 2.100, 2.200, 2.300, 2.400, 2.500, 2.600, 2.700, 2.800, 2.900, 3.000, 3.100, 3.200, 3.300, 3.400, 3.500, 3.600, 3.700, 3.800, 3.900, 4.000, 4.100, 4.200, 4.300, 4.400, 4.500, 4.600, 4.700, 4.800, 4.900, 5.000, 5.500, 6.000, 6.500, 7.000, 7.500, 8.000, 8.500, 9.000, 9.500, and/or 10.000 mm, and all ranges of the above.

The cross sectional shapes of the channels are not particularly limited. In some embodiments the cross section of the channels include, but are not limited to, sinusoidal, circular, elliptical, and other shapes. In some embodiments these channels may be straight and/or curved, they may intersect or not intersect, they may converge or diverge, and they may be of uniform depth or of varying depths along their length.

Without being bound by theory or mechanism, channels can provide porosity for bony ingrowth. Additionally, in some implementations the decreased cross sectional area at the tops of the protuberances can cause the allograft to elastically deform under dynamic compressive loading, thereby causing the channels to temporarily decrease in height. Without being bound by theory or mechanism, this cyclic shortening of the channels may provide a mechanical stimulus (e.g., micromotion) to the subject's host cells to promote bone growth within the channels due to Wolff's Law of Bone Remodeling.

In some embodiments the channels are configured such that top sections of some or all of the channels are coplanar and thus form an imaginary plane, referred to herein as the "channel plane." In some embodiments, a channel plane and a flat plane mate for dynamic compression between the two. In other embodiments, a channel plane and another channel plane mate for dynamic compression between the two. In some embodiments, a channel plane and a flat plane (e.g., host bone surface) mate for dynamic compression between the two. In yet other embodiments, the top sections of the channels are not coplanar.

In some embodiments, channel planes or flat planes of multiple protuberances may be coplanar. In some embodiments, channel planes or flat planes of multiple recesses may be coplanar. In some embodiments, channel planes or flat planes of multiple protuberances may not be coplanar. In some embodiments, channel planes or flat planes of multiple recesses may not be coplanar.

Additionally, in some embodiments a vertical wall profile and an overhang feature of the vertical wall profile allow for dynamic compressive motion between the components. Additionally, in some embodiments the presence of the overhang limits mated components from separating beyond the overlap of the two overhang features.

Additional features and advantages of the systems and methods of the present disclosure will become evident to those of ordinary skill in the art after a study of the description, figures, and non-limiting examples in this document.

One embodiment of the present invention an implant, comprising a body comprising at least a top piece and a bottom piece that have mating interlocking surfaces that couple the pieces together as one piece, the body comprising a front side, back side, top side, bottom side, anterior side, posterior side, and a length extending from the anterior side to the posterior side; the top piece and the bottom piece each having a superior/upper surface and an inferior/lower surface, wherein at least a portion of the inferior surface of the top piece engages with the superior surface of the bottom piece when the top piece and the bottom piece are coupled together; the top piece and the bottom piece each comprising at least two protuberances and corresponding complimentary recesses to receive the protuberances from a second piece; said protuberances comprising radii along its height and said recesses comprising radii along its depth; wherein at least part of the top piece inferior surface and at least part of the bottom piece superior surface comprises ridges that form channels across the respective surfaces, the channels providing intermittent distances between the respective surfaces.

Another embodiment of the present invention is at least a three-piece implant that comprises a body comprising at least a first top piece, at least one second top piece/middle piece, and a bottom piece that have mating interlocking surfaces that couple the pieces together as one piece, the body comprising a front side, back side, top side, bottom side, anterior side, posterior side, and a length extending from the anterior side to the posterior side; the first top piece, second top piece, and the bottom piece each having a superior/upper surface and an inferior/lower surface, wherein at least a portion of the inferior surface of the top piece engages with a portion of the superior surface of the second top piece, and at least a portion of the inferior portion of one of the at least one second top piece engages with at least a portion of the superior surface of the bottom piece when pieces are coupled together; the top piece comprising at least two recesses; the second top piece comprising at least two protuberances on the superior surface that correspond with and are received by complimentary recesses of the top piece when engaged with the top piece, and at least two protuberances on the inferior surface; the bottom piece comprising at least two corresponding recesses that are complimentary to and receive the protuberances from a second top piece when engaged; said protuberances comprising radii along its height and said recesses comprising radii along its depth; wherein at least part of the surfaces comprising protuberances comprise ridges that form channels across the respective surfaces, the channels providing intermittent distances between the respective surfaces when engaged.

Another embodiment of the present invention is a kit that comprises at least one top piece and at least one bottom piece as described herein.

BRIEF DESCRIPTION OF THE DRAWINGS

FIGS. 5 and 6 illustrate a side view of complimentary top pieces and bottom pieces of embodiments of the present invention.

FIG. 8 provides a view of two component pieces of a composite bone graft according to the present disclosure.

FIGS. 14 and 15 illustrate an aspect of testing shown in the Example, below. Included is a diagram of the compression testing showing the mating sections were rotated 60 degrees from the vertical plane. This resulted in a normal force, $F_N$, between the mating sections and a shear (transverse) force, $F_T$, between the mating sections that was one half of the normal force.

DETAILED DESCRIPTION OF THE EXEMPLARY EMBODIMENTS

Figure 1:
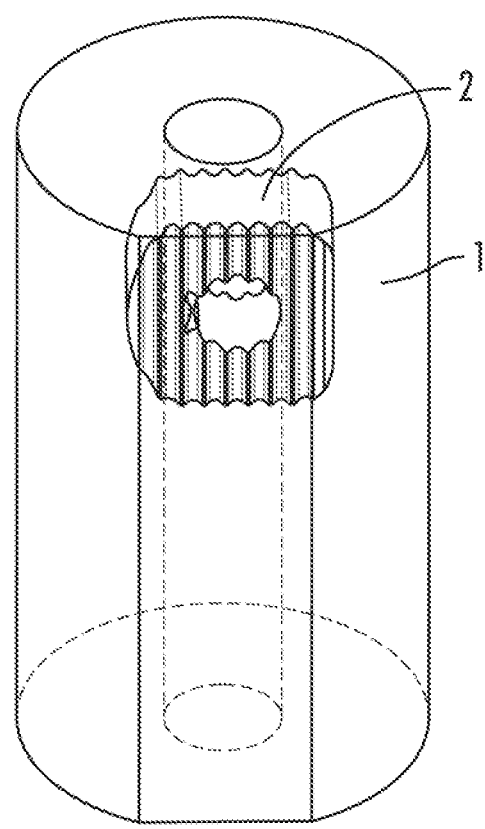
FIG. 1 illustrates a conical bone segment 1, including a location from which an allograft, in this case a cervical allograft 2, may be cut.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Each example is provided by way of explanation of the present disclosure and is not a limitation thereon. In fact, it will be apparent to those skilled in the art that various modifications and variations can be made to the teachings of the present disclosure without departing from the scope of the disclosure. For instance, features illustrated or described as part of one embodiment can be used with another embodiment to yield a still further embodiment.

All references to singular characteristics or limitations of the present disclosure shall include the corresponding plural characteristic(s) or limitation(s) and vice versa, unless otherwise specified or clearly implied to the contrary by the context in which the reference is made.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a bone" includes a plurality of bones, and so forth.

All combinations of method or process steps as used herein can be performed in any order, unless otherwise specified or implied to the contrary by the context in which the referenced combination is made.

The methods and systems of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing quantities, properties, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

While the following terms used herein are believed to be well understood by one of ordinary skill in the art, definitions are set forth to facilitate explanation of the presently-disclosed subject matter.

As used herein, the terms "graft" and "tissue graft" are used interchangeably to generally refer to any transplant or transfer of body materials. The term graft is inclusive of, but is not limited to, allografts, xenografts, autografts, and the like. Material transplanted from one subject's body to another (i.e., within the same species) is termed as allograft (e.g. cornea transplant from one human to another); material transplanted from one species to an animal of another species is termed a xenograft (e.g., heart valves from a pig transplanted to a human.) Furthermore, autograft is tissue transplanted within one individual (auto-meaning "self"). A clinical example would be treating a burn patient with his or her own skin taken from another location on the body.

In some embodiments, the bone graft(s) of the present disclosure is preferably but not necessarily of human origin. Those of ordinary skill will also appreciate that the term graft, as used herein, is inclusive of various different grafts, such as cortical and/or cancellous bone grafts, ligament tissue grafts, tendon tissue grafts, conical cartilage tissue grafts, organ tissue grafts, skin tissue grafts, and the like. In some instances a graft will become calcified, ossified, incorporated, and/or vascularized after being implanted in a subject. Moreover, the grafts of the present disclosure may include aseptically processed grafts, which may have been preserved in refrigerated or frozen conditions.

In some instances, a graft is implanted into a subject in need thereof to treat a particular condition and/or disease. The method comprises providing at least one composite implant, according to the present disclosure, to a subject in need thereof at an implantation site. In various aspects, a composite implant can be administered therapeutically; that is, administered to treat an existing disease or condition. In further various aspects, a composite implant can be administered prophylactically; that is, administered for prevention of a disease or condition.

The terms "subject" or "subject in need thereof" refer to a target of administration and/or implantation, wherein the subject optionally displays symptoms related to a particular disease, pathological condition, disorder, or the like. The subject of the herein disclosed methods can be, for example, a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term "subject" does not denote a particular age or sex. Thus, adult and newborn subjects, as well as fetuses, whether male or female, are intended to be covered. A "subject" refers to a subject afflicted with a disease or disorder. The term "subject" includes human and veterinary subjects.

The terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder and/or resulting symptoms of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Thus, turning to the invention(s) of the present disclosure, in the medical device industry, CNC machining has revolutionized companies' abilities to develop and manufacture innovative products for many different therapeutic and diagnostic devices. One significant use of CNC machining for medical devices was for the manufacture of injection molds that were used primarily for making small plastic components.

While many medical device companies adopted CNC machining to manufacture orthopedic implants in the late 1970s, 1980s and early 1990s, tissue banks, which process donated human tissue for transplant, began to adopt CNC milling in the late 1990s and early 2000s for machining human cortical bone. CNC machining has been primarily used for the production of allografts utilized in spine surgery, and now other areas, such as foot and ankle reconstruction and trauma, are also seeing allografts manufactured with this technology.

Over the last 15 years, increasingly more tissue banks have implemented CNC machining as a method to manufacture cortical bone allografts, because it is fast, efficient, and cost-effective, it provides for a high level of repeatability and reproducibility and can form geometrically complex allografts. Traditionally, processing cortical bone allografts required that they be cut by hand on band saws, with oscillating saws, with hand drills, and/or with other handheld and bench-mounted equipment. These manufacturing procedures often utilized complex fixtures to hold irregular-shaped pieces of bone to create angled cuts and to put ridges (referred to as teething and castling) in the top and the bottom of the allograft. These known tissue processing methods have a low level of reproducibility and repeatability.

While the manufacturing processes were gradually advancing, the material technology was also evolving to meet the specific surgical needs in terms of mechanical and biological properties. Ideally, a material to be used as a structural implant would have an elastic modulus very close to the host tissue in the surgical site, in this particular case, human bone.

Medical devices (implants) were developed for various applications in the spine that were initially made of cobalt-chrominum superalloys, stainless steel, and later commercially pure and alloyed titanium. In the 1990's carbon fiber reinforced polymer (CFRP), polyether ether ketone (PEEK), some ceramics, and porous tantalum were also added to this list of materials.

Cortical bone allograft in the spine for structural interbody support and for posterolateral fusion has been used since the 1970's. Prior to that time, autogenous iliac crest blocks were often used as structural interbody support for spinal fusion. (See Smith, Robinson).

During the surgical procedure, the surgeon would cut the bone allograft, often a piece of femur, humerus, fibula, radius, ulna, or iliac crest to the desired size and shape for the surgical site. In spinal fusion procedures in which the intervertebral disc was removed and the neural elements were decompressed, femoral ring allografts (or conical bone rings from other bones) or sections of iliac crest or blocks of cancellous bone were often used for structural interbody support in the disc space for the fusion. Autologous morsellized bone from the surgical site or the iliac crest was then used as the biological component and filled into the intramedullary canal of the conical ring allograft (or around the allografts) to help promote the fusion mass to unite the two vertebrae.

Likewise, tricortical iliac crest autografts and allografts were used in the spine whereby cutting and contouring by the surgeon was required. To present, this is still often the case with allogeneic iliac crest and to a lesser extent autogenous iliac crest (because the surgical harvestation of autologous tricortical iliac crest blocks can cause significant morbidity at the recovery site and thus the procedure is not as common as it was in the past).

Some advantages of using conical bone as a structural material over other implant materials (metals, ceramics and polymers) are that conical bone serves as a harmonious biological and mechanical scaffold for which (i) host bone fusion mass can incorporate onto and into the allograft, (ii) bone allografts have an elastic and shear modulus much closer to the subject's own bone at the surgical site, and (iii) it acts as a structural entity to maintain the disc height (vertebral spacing) and alignment while the fusion between the vertebrae progresses.

Historically, the disadvantages of cortical bone ring allografts were the inconsistencies in size and shape. The human femur is a relatively round shape in many instances and has an average diameter of about 24 to about 32 mm, so it lends itself well for use as an allograft in the anterior lumbar interbody fusion (ALIF) spinal procedure. The humerus is often too large for use as structural interbody support in the cervical spine and fibula, radius and ulna although often the right size "range" have inconsistent shapes. Bones have large variations in terms of size and shape depending on the relative health, age, weight, sex, activity level, past medical history, etc. of the subject from whence they are derived.

Because of these geometrical limitations and the fact that a surgeon has to cut and contour the bone to fit a subject's spine, allograft bone used as structural interbody support has been considered by those in the art to be a compromise in comparison to an implant because the size and shape of an implant is always known up front, whereas typically, traditionally processed allografts vary, at least dimensionally, from graft to graft.

CNC milling technology has been adopted as a way to precisely machine human cortical bone in order to create reproducible and repeatable structural allografts. This provides a means to make allografts of specified geometries and/or sizes for different footprints (profiles) and also as a way to create allografts with graduated heights in, for example, about 1 and/or 2 mm increments for a surgeon to select the allograft that would best fit in a subject's prepared spinal disc space or other prepared surgical site. This is often accomplished using surgical instruments designed for the allografts. In this way, many cortical bone allografts are presented in the operating theatre in the same way as would be implants made of titanium, PEEK, or other materials.

Because of the implementation of CNC milling technology into the processing of human cortical bone allografts, specific surgical instruments may be developed for the implantation of one type of allograft or another. In manufacturing these allografts in such a manner, tissue banks could then provide cortical bone allografts with the engineering design of implants along with the mechanical and biological benefits of human cortical bone. In other words, the CNC-machined allografts, in conjunction with the specific surgical instruments that are developed for them, are becoming more and more like implants made of metal or plastic. Thus, in creating these specialized allograft lines, tissue banks have become increasingly sophisticated in their ability to engineer, design and manufacture cortical bone allografts.

Indeed, many tissue banks have implemented CNC machining systems to manufacture cortical bone allografts because CNC machining is cost-effective and provides for a high level of dimensional repeatability and reproducibility. For example, this has been applied to the manufacture of spinal allografts that act as structural interbody support for use in spinal fusion. The technology is now being applied to the production of allografts for other areas of orthopedic surgery and other types of surgery as well.

Although the use of CNC machining is a significant manufacturing improvement for tissue banks, as it has been for many industries, the geometric limitations of human conical bone (both size and shape) still limit a tissue bank's ability to make allografts of every size and shape that would have good utility to act as a structural or non-structural allograft for each and every desired surgical procedure.

The present disclosure addresses these and other problems known in the art by providing, in exemplary embodiments, multiple allograft component pieces, each comprising bone, such as cortical bone, that may be cut or otherwise manipulated by CNC machining (or by other machining processes) and then fitted and/or connected together to assemble a larger composite bone graft, wherein the composite bone graft may be prepared for insertion and/or implantation into a subject.

In certain embodiments, the composite bone graft of the present disclosure comprises one or more cortical bone components/pieces, which may be assembled together to form the composite bone graft. And in certain embodiments, the composite bone graft may comprise a finished allograft or an in-process allograft that can then be further machined.

Indeed, in some embodiments of the present disclosure, bone pieces comprising cortical and/or cancellous bone are assembled and/or connected together to form a composite bone graft, such as a composite autograft or allograft.

In certain embodiments, two or more layers and/or component pieces comprising bone are joined together to achieve a total desired cortical thickness, desired lordosis (the angle between the superior and inferior surfaces of the graft used to recreate the natural curvature of the spine) and total desired footprint (platform size) and to create composite grafts, such as spinal grafts, that could not previously be achieved with the available anatomy in the cortical bone found in the shafts of long bones of a subject.

Indeed, in an exemplary embodiment, component pieces of bone connect together to form a composite bone graft due to the complementary geometry of the two or more component pieces that comprise a composite bone graft. In certain embodiments, one or more component pieces of a composite bone graft includes a portion of a conical wall of at least one bone. Yet, the size (thickness) of grafts that can be generated by the present disclosure may be limited, in some embodiments, by the cortical walls that are found in certain shafts.

Because of the variance in size and shape and the dimensional limitations of donor bone, such as human bone, from which to process grafts, it is advantageous to provide a system in which one or more pieces of bone can be connected together, attached and/or otherwise held together to create an allograft that would be impossible and/or difficult to manufacture out of a single piece of donor bone. Accordingly, the present disclosure provides, in some embodiments, a composite bone graft comprising at least one component piece derived from a first donor and at least one component piece derived from a second donor, wherein each component piece may comprise cortical bone. In further embodiments, a composite bone graft according to the present disclosure comprises at least one component piece derived from a first bone collection site and at least one component piece derived from a second bone collection site, wherein the component pieces may be collected from one or multiple donors, simultaneously or asynchronously, and further wherein the component pieces may be joined and/or connected together to produce the composite bone graft.

As such, in an exemplary embodiment, the present disclosure provides a system that comprises component graft pieces that may be combined to produce a larger, composite graft. In some embodiments, the component pieces comprise a varying geometry and/or landscape of protuberance(s) and/or recesses on at least one surface that allows for complementary pieces of bone graft material to connect and/or interlock (e.g. snap together) and remain connected and/or locked together to at least one other component piece due to the particular geometry of the protuberance and/or recesses. Each component piece may comprise bone material and may have its own unique geometry in some embodiments. In other embodiments, two or more component pieces having an identical or nearly identical geometry may be joined to form a composite graft.

In some embodiments, a first component comprises a first face with a first set of projections thereon, the first face being arranged in such a manner relative to a second set of projections of a second face of a second component that the distance between a terminal end of at least one projection of the first set of projections to the first face is less than or equal to the maximum distance between a terminal end of at least one projection of the second set of projections to the second face.

Indeed, the present disclosure provides, in certain embodiments, component pieces comprised of bone, such as conical bone, that can be connected together by means of projections and/or recesses, extending and/or receding from at least one surface, respectively, of at least two component pieces. The component pieces may be arranged so as to allow the engagement of protruding and/or recessed portions of an adjacent component, such that a composite graft may be assembled from the component pieces. Further, one can select a properly sized and shaped composite implant for each subject and/or each procedure.

In some embodiments, the present disclosure is directed to a system comprising at least two component pieces of a composite bone implant system, wherein a first component piece may be connected, attached, and/or joined to a second component piece to form a composite bone implant. In some embodiments, a releasable connection is established between at least one surface of the first component and at least one surface of the second component when the projections of the first component are interdigitated relative to the projections of the second component. In other embodiments, a permanent connection is established between a first component and a second component to form a composite graft.

Unlike implantable plastics or metals, human bone has both size and shape limitations. Thus, when working with a donor, the amount of available working material is limited. As an example, FIG. 1 shows a configuration, wherein the bone 1 for a cervical allograft 2 (shown in final form), is taken from a femur segment. In some embodiments, a graft material, such as that shown in FIG. 1 may have, for example, an 11 by 14 mm footprint. Moreover, the maximum height of a graft material taken from a donor is limited by the shape, local radius, and/or cortical wall thickness of the segment of the long bone at a donation site. As shown in FIG. 1, a defined maximum height can be attained with a graft of this type and size. In some embodiments, a graft machined by this method may be, for example, approximately 11 mm depth and 14 mm wide and 10 mm height with the final height of the allograft being determined in large part by the cortical wall thickness.

As indicated herein, the present invention provides an exemplary embodiment of two bone component pieces. In embodiments, each of the component pieces (which may be two, three, four, five, six, or more) comprise at least one surface (or face) that is complementary to at least one surface (or face) of an adjoining piece, wherein the projections provided on each of the components may be interdigitated with those of the other such that the two component pieces can be connected and/or joined to form a composite graft. In some embodiments, each component piece comprises bone. And in certain embodiments, the composite graft is a bone graft, which may be, for example, an autograft or an allograft. While the component pieces are generally about the same in size and/or geometry, the dimensions of component pieces may be selected as desired by a physician or other clinician for a particular application.

In some embodiments of the present disclosure, component pieces of a composite graft may comprise the same geometry or essentially the same geometry. In other embodiments, the component pieces may connect and/or interlock but may have different geometry. In some embodiments, at least one component piece in a pair of complementary component pieces has a profile of projections that is the same as those on at least one other component piece.

Figure 2:
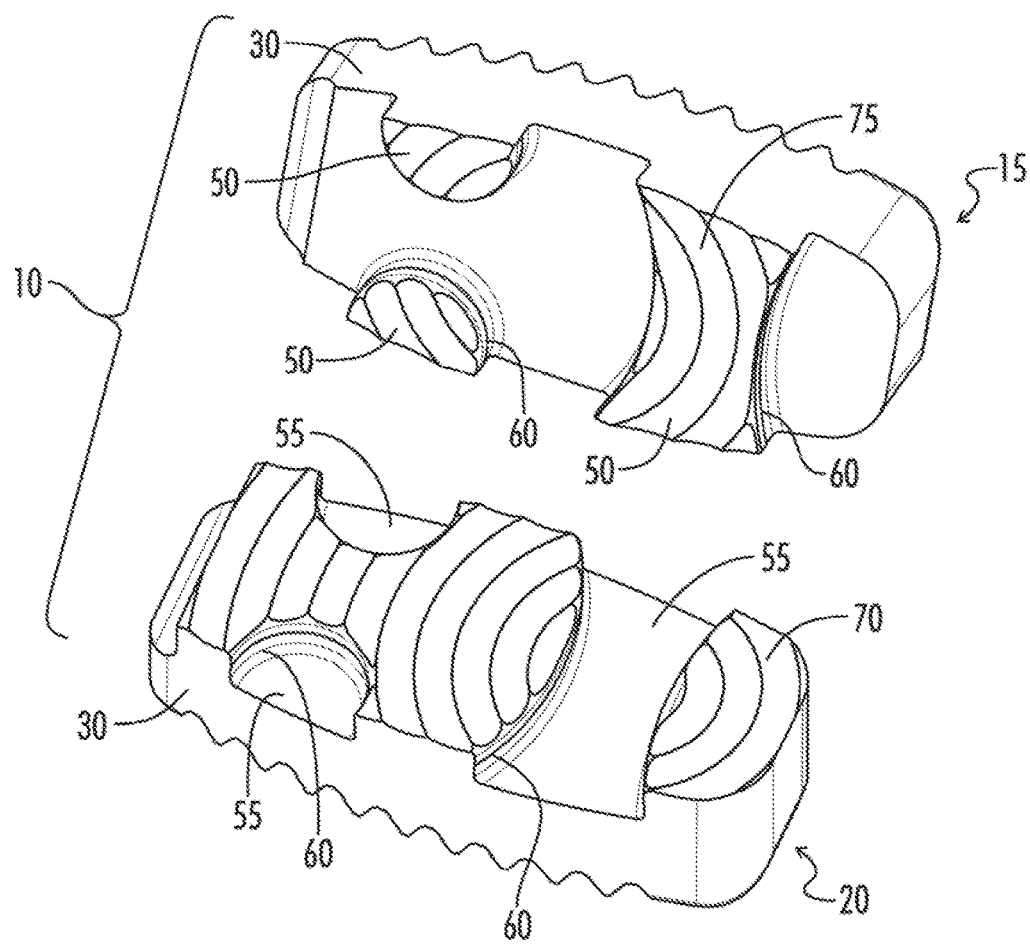
FIG. 2 illustrates an exemplary configuration of two bone component pieces that are useful in the methods of the present disclosure, specifically an implant top piece and an implant bottom piece.
Figure 3:
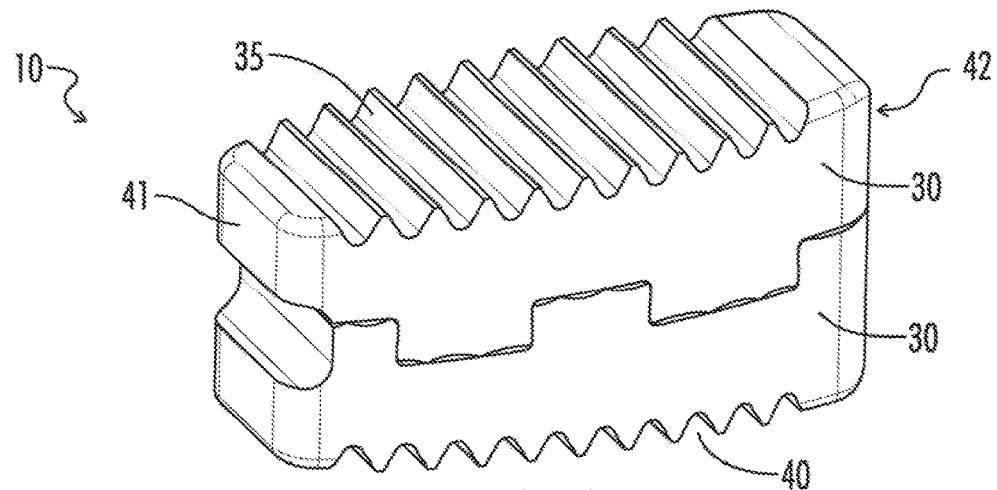
FIG. 3 illustrates an embodiment as shown in FIG. 2, wherein a top piece is engaging a bottom piece.
Figure 4A:
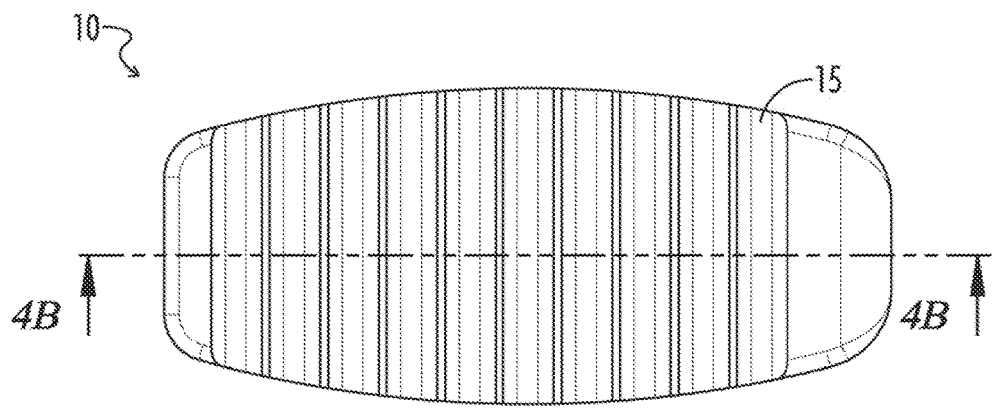
FIG. 4A illustrates a top surface of an exemplary implant of the present invention.
Figure 4B:
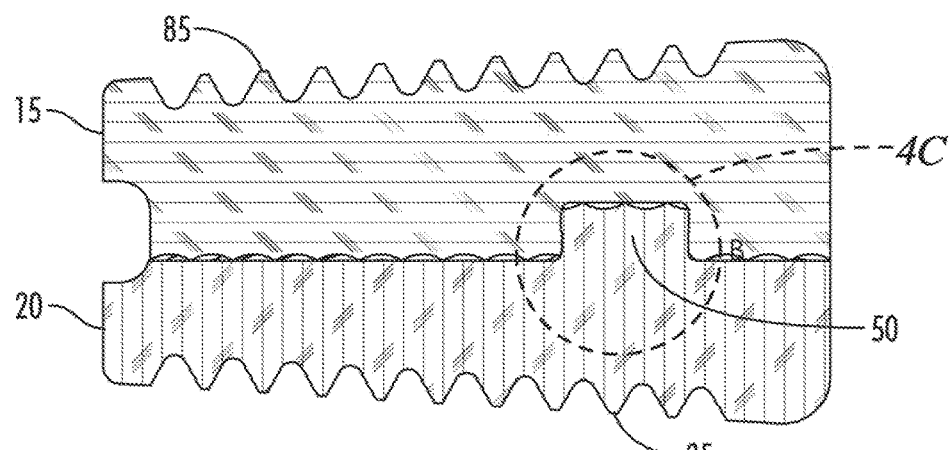
FIGS. 4B and 4C illustrate a cross sectional view of the assembled two component composite bone graft shown in FIG. 4A.
Figure 4C:
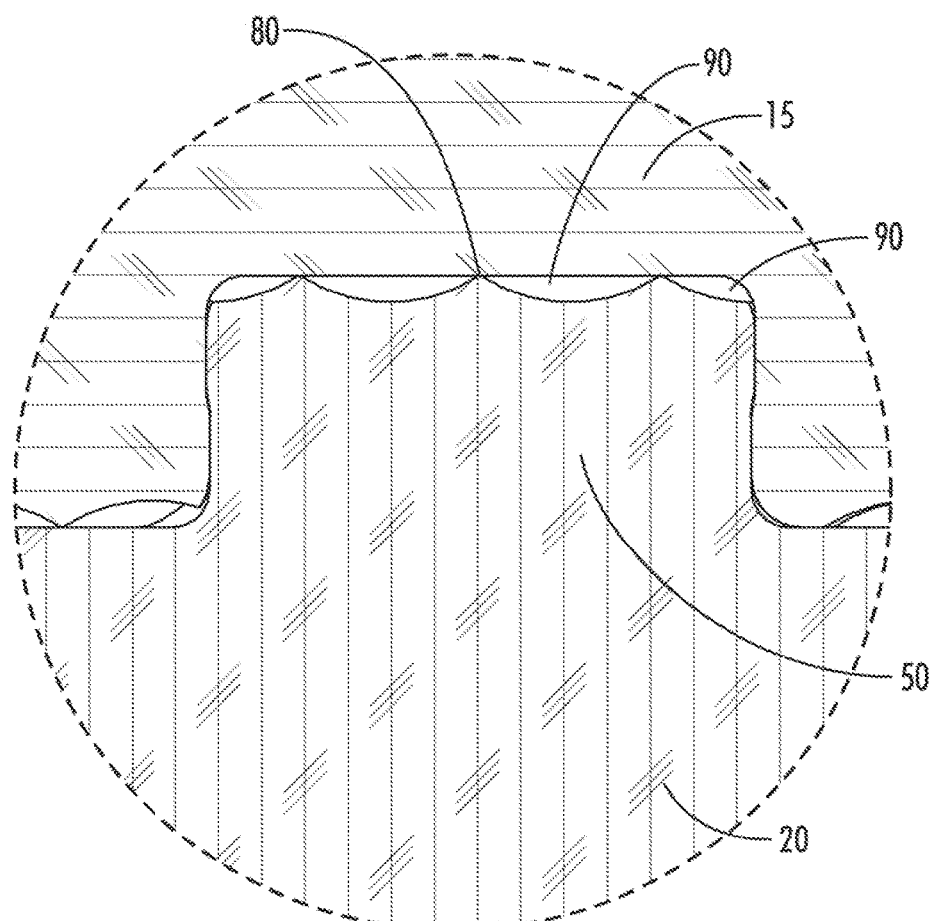
Figure 7:
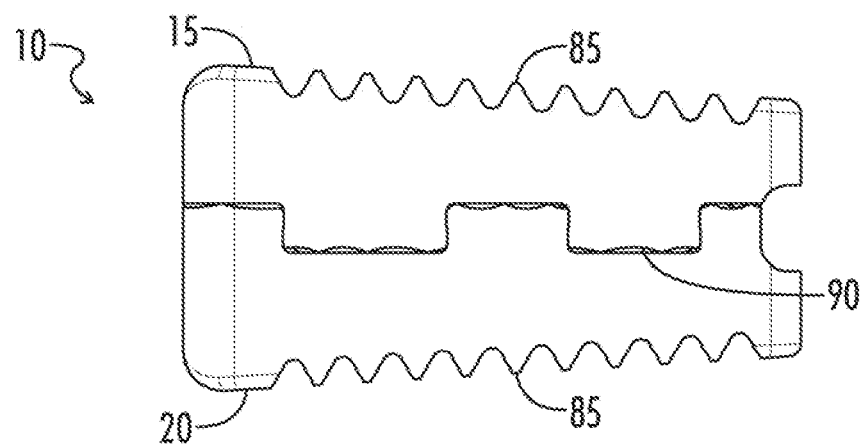
FIGS. 7 and 8 illustrate two component pieces of a composite bone graft according to the present disclosure engaging one another.
Figure 8:
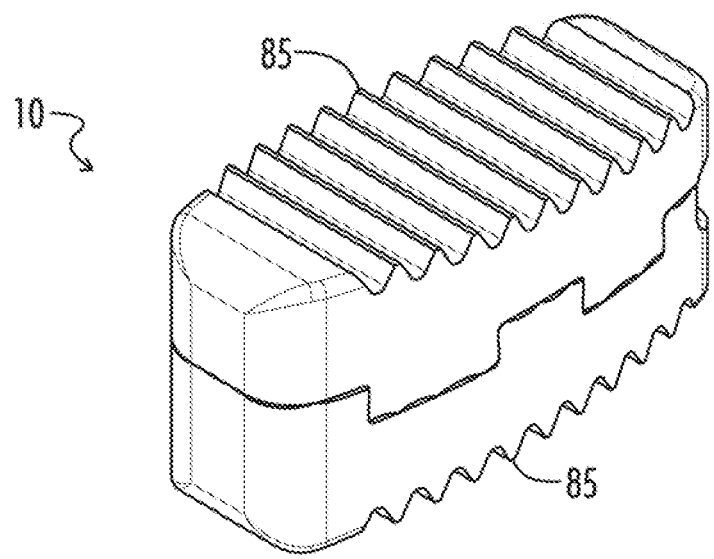

FIG. 2 shows an implant of the present invention. The body 10 of this embodiment comprises a top piece 15 and a bottom piece 20 that have mating interlocking surfaces that couple the pieces together as one piece. The body 10 has a back side 30, front side, top side 35, bottom side 40, posterior side 41, anterior side 42, and a length extending from the anterior side to the posterior side. This embodiment is generally rectangular, but the present invention is certainly not limited by shape. Additionally, embodiments of the present invention can be assembled and then further milled into a variety of shapes, such as a dowel shape or screw-shaped.

Each piece has a superior/upper surface 70 and an inferior/lower surface 75. When the pieces are engaged or coupled together, a portion of the inferior surface of one piece engages with the superior surface of the second piece.

The pieces each comprise at least two protuberances 50 and recesses that are complimentary to the protuberances from a second piece. The protuberances comprising radii 60 along its height, or wall. The recesses also comprising radii 60 along their depth.

Additionally, in embodiments, parts of the top or first piece inferior surfaces and parts of the bottom piece superior surfaces comprises ridges that form channels 90 across the respective surfaces. These channels provide intermittent distances between the respective surfaces. These channel planes are described above and can provide porosity for bony ingrowth As shown in the figures, the superior surface of the top piece and the inferior surface of the bottom piece may comprise ridges 85. These ridges, or teething, serves to resist implant migration, provide more surface area for host-bony ingrowth, and allow for some settling of the vertebrae to create a conforming fit between the superior and inferior vertebrae with the allograph/implant between the two.

Figure 9:
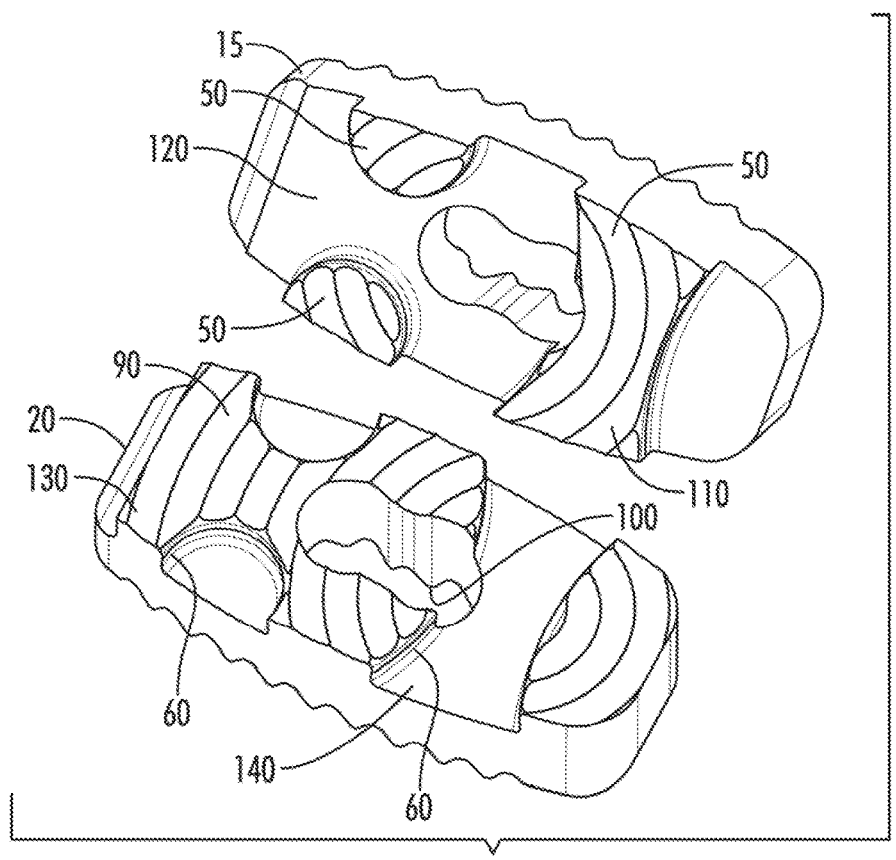
FIG. 9 illustrates an exemplary configuration of two bone component pieces that are useful in the methods of the present disclosure, specifically an implant top piece and an implant bottom piece. Shown in this embodiment is an implant with a common hollow interior space.
Figure 10:
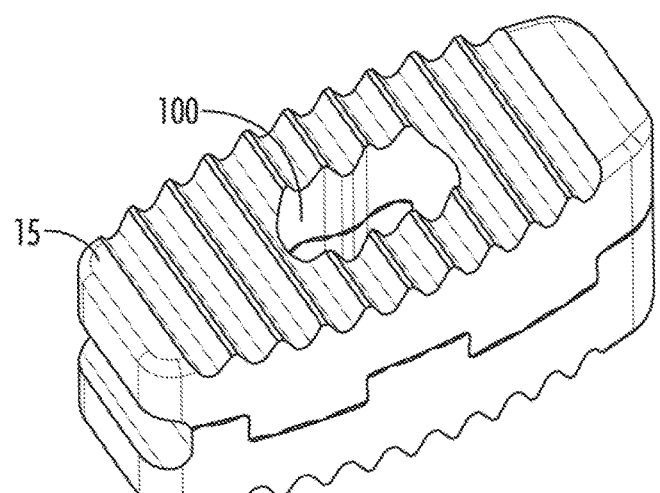
FIG. 10 provides another view of an exemplary embodiment of an assembled composite bone graft of FIG. 9.

As shown in FIGS. 9 and 10, for example, the pieces, when engaging one another, form a common hollow interior space 100 that is generally perpendicular to the inferior and superior surfaces. This common interior space is adapted to receive at least one of osteoconductive material, osteoinductive material, osteogenic material, a pharmaceutical, osteobiologic material and any combination thereof.

In embodiments of the present invention, the common edge of a side and an end are chamfered, which in some cases may improve the ease at which the implant is inserted into the surgical site.

The present invention is virtually unlimited in the range of various shapes of the protuberances and corresponding recesses. For example, the a protuberance and corresponding recess may be circular or partially circular, sinusoidal or partially sinusoidal, parabolic or partially parabolic, elliptical or partially elliptical, round, concave, biconcave, pianoconcave, convex, biconvex, or piano-convex. Thus is such to resist shear in multiple directions.

The protuberance may completely span from the front surface of a piece to the back surface of a piece. Additionally, the protuberance may border an edge/side or the common hollow space.

The implants of the present invention can comprise a wide variety of implantable materials such as, for example, cortical bone, cancellous bone, titanium, carbon fiber, tantalum, stainless steel, cobalt chromium, polyetheretherketone (PEEK) polymer, and any combination thereof. The bone material may be partially or fully demineralized.

As indicated above, the implant can comprise two, three, four, five, or more pieces. Thus, the implant can comprising a second top piece 16 that has a superior surface with protuberances and recesses that correspond with the inferior surface of the first top piece, and has an inferior surface with protuberances and recesses that correspond with the superior surface of the bottom piece. In this embodiment, the second top piece may have recesses on the superior and inferior surfaces to intermittently engage the adjacent surfaces of the first top piece, and additional top piece, or the bottom piece. Likewise, the first top piece inferior surface can comprise an upper machined surface 110 and a lower machined surface 120 defined by the height (wall height) of the protuberances; and second top piece can comprise an upper machined surface and a lower machined surface defined by the height of the protuberances; and the bottom piece superior surface can comprise an upper machined surface 130 and a lower machined surface 140 defined by the height of the protuberances. Likewise, when the protuberances comprises ridges 80, the lower machined surfaces may substantially flat such that the recesses intermittently engage the lower machined surfaces.

Another embodiment of the present invention is an implant comprising a first top piece 15, at least one second top piece/middle piece 16, and a bottom piece 20 that have mating interlocking surfaces that couple the pieces together as one piece, the body comprising a front side, back side, top side, bottom side, anterior side, posterior side, and a length extending from the anterior side to the posterior side; the first top piece, second top piece, and the bottom piece each having a superior/upper surface and an inferior-lower surface, wherein at least a portion of the inferior surface of the top piece engages with a portion of the superior surface of the second top piece, and at least a portion of the inferior portion of one of the at least one second top piece engages with at least a portion of the superior surface of the bottom piece when pieces are coupled together. The top piece may comprise at least two recesses 55. The second top piece comprising at least two protuberances 50 on the superior surface that correspond with and are received by complimentary recesses 55 of the top piece when engaged with the top piece, and at least two protuberances on the inferior surface. The bottom piece comprising at least two corresponding recesses 55 that are complimentary to and receive the protuberances from a second top piece when engaged. The protuberances comprising radii along its height and said recesses comprising radii along its depth. The at least part of the surfaces comprising protuberances comprise ridges that form channels 90 across the respective surfaces, the channels providing intermittent distances between the respective surfaces when engaged.

Figure 11A:
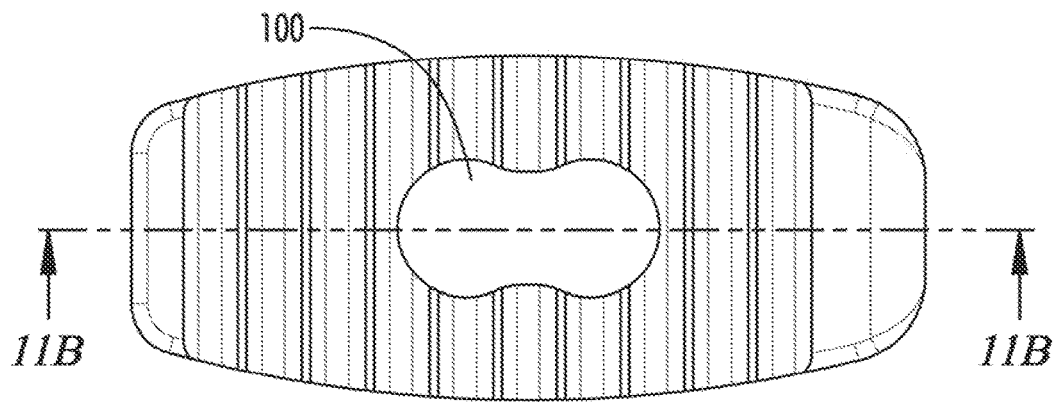
FIG. 11A shows the top view of an embodiment of the present invention. Shown in this embodiment is an implant with a common hollow interior space.
Figure 11B:
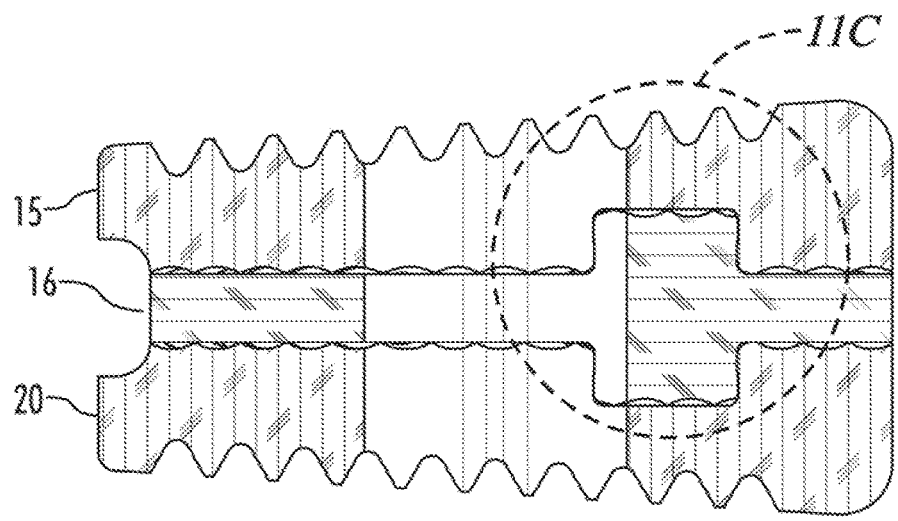
FIGS. 11B and C show side views of the embodiment of FIG. 11A. Shown in this view is a three-piece assembly.
Figure 11C:
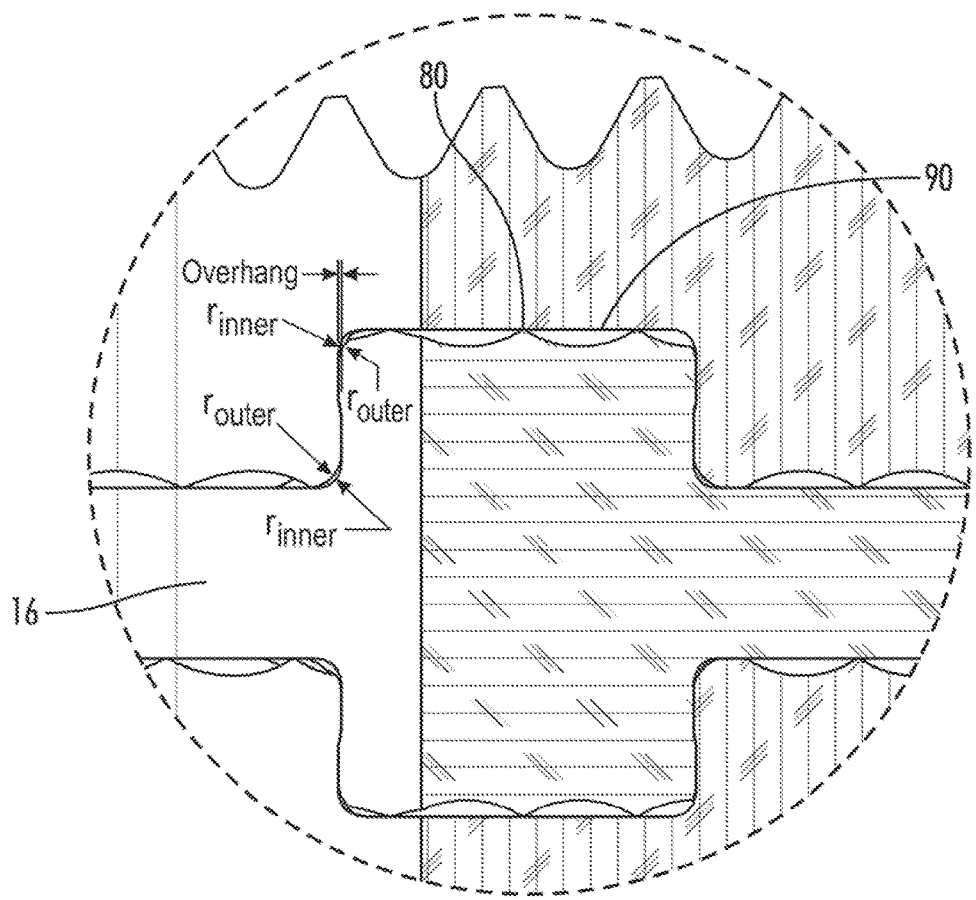
Figure 12:
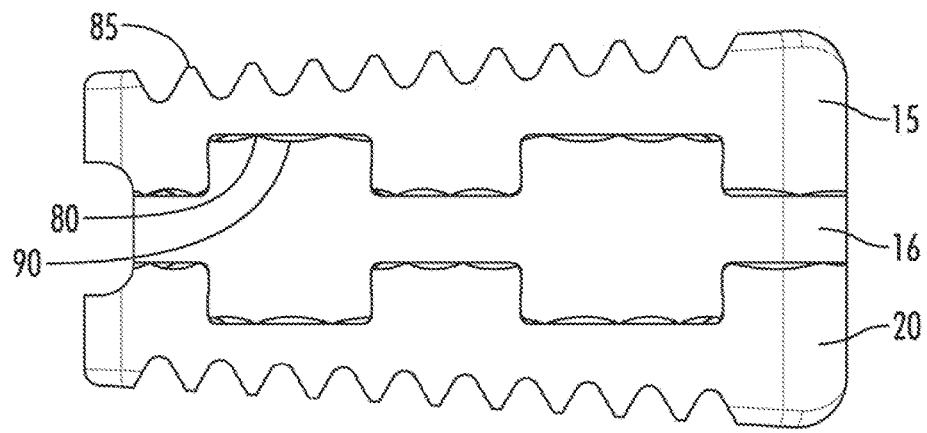
FIG. 12 shows a side view of an example of a three-piece implant of the present invention.
Figure 13:
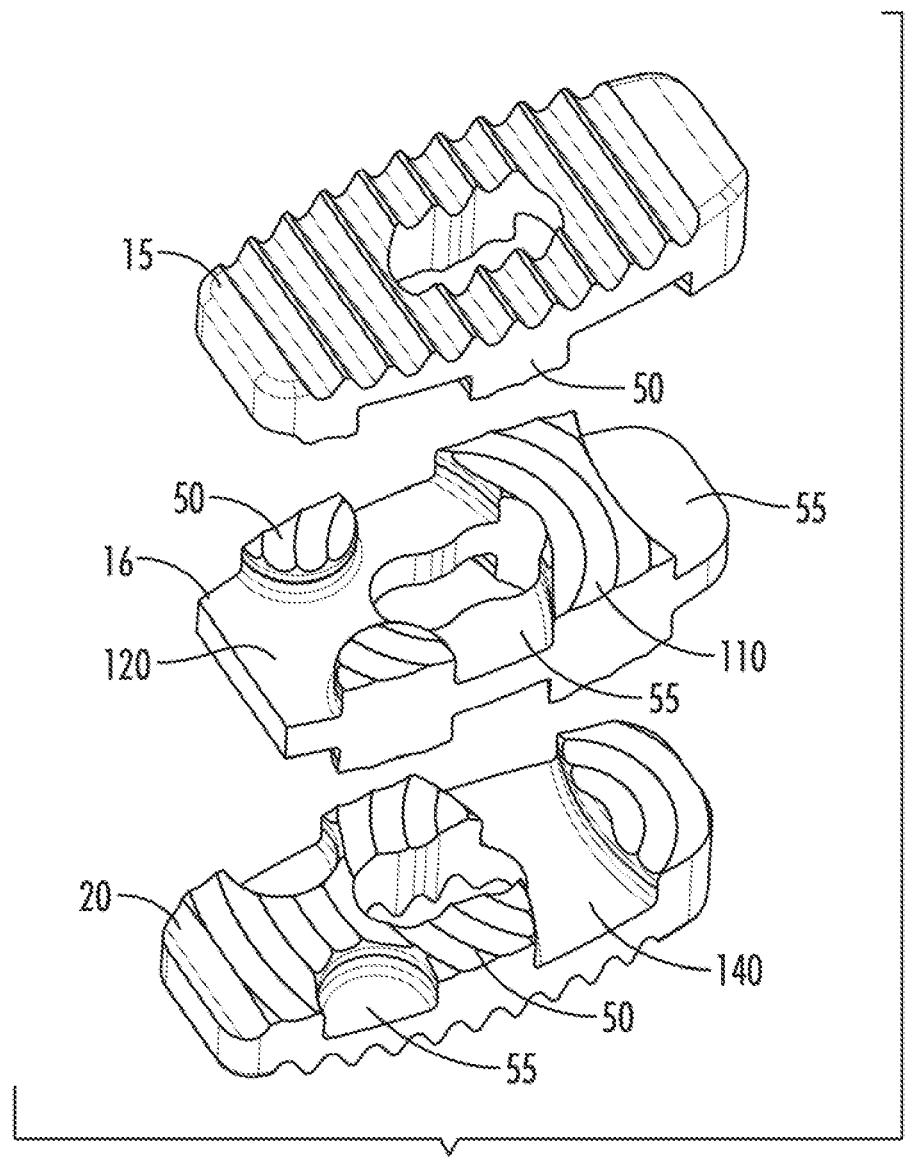
FIG. 13 shows an exploded view of an un-engaged embodiment of a three-piece implant of the present invention.

FIG. 11C provides views of a profile of an exemplary component having a wall with an overhang that causes, for example, two components to connect and/or be locked together. In some embodiments, the wall, such as that shown in FIG. 11C, is a vertical wall profile. Indeed, the exemplary embodiment shown in FIG. 11C comprises an overhang feature. Specifically, in FIG. 11C, an overhang is provided in approximately the middle of a central section of a vertical wall. Note the inner and outer radii on the bottom and top of the wall respectively.

In order to create the vertical wall profile with the inner and outer radii and the overhang of the invention, a series of CNC cutting steps can be utilized to create the full profile. In some embodiments, the profile is designed so that a wall profile of two mating pieces will interlock with each other and hold together under a reasonable amount of, for example, shear force, tensile force, and/or compressive force. In some instances shear force to load to failure is about 40, 42, 44, 46, 48, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5200, 5400, 5600, 5800, 6000, 6200, 6400, 6600, 6800, 7000, 7200, 7400, 7600, 7800, 8000, 8200, 8400, 8600, 8800, 9000, 9200, 9400, 9600, 9800, 10000, 11000, 12000, 13000, 14000, 15000, 16000, 17000, 18000, 19000, to about 20000 Newtons. Furthermore, in some instances the force required to separate the allograft components in tension is about 20, 22, 24, 26, 28, 30, 32, 34, 36, 38, 40, 42, 44, 46, 48, 50, 55, 60, 65, 70, 75, 80, 85, 90, 95, 100, 110, 120, 130, 140, 150, 160, 170, 180, 190, 200, 220, 240, 260, 280, 300, 320, 340, 360, 380, 400, 420, 440, 460, 480, 500, 550, 600, 650, 700, 750, 800, 850, 900, 950, 1000, 1100, 1200, 1300, 1400, 1500, 1600, 1700, 1800, 1900, 2000, 2200, 2400, 2600, 2800, 3000, 3200, 3400, 3600, 3800, 4000, 4200, 4400, 4600, 4800, 5000, 5200, 5400, 5600, 5800, 6000, 6200, 6400, 6600, 6800, 7000, 7200, 7400, 7600, 7800, 8000, 8200, 8400, 8600, 8800, 9000, 9200, 9400, 9600, 9800, to about 10000 Newtons.

In conducting some methods of the present disclosure, by utilizing CNC machining technology, the inventors of the present disclosure have created complex component shapes/pieces of cortical bone that may be assembled to produce composite implants. Embodiments of the present grafts can include complex paths of the profile of the mating surfaces. In some embodiments, the component shapes and/or composite bone implants of the present disclosure are CNC-machined allografts. In some embodiments, the components and/or composite bones of the present disclosure are surgically advantageous, as they provide advantages over non-machined pieces of human bone. Further, in certain embodiments, the present disclosure provides components and/or composite implants comprising any one or more of bone, titanium, carbon fiber or other implantable material, or any combination thereof.

In an embodiment, two component pieces of a composite implant are identical. In this embodiment, the design of each component is relatively symmetric across its length and from front to back.

Of course, in other embodiments, the component pieces of a composite implant do not have the same geometry and therefore are not symmetrical around a particular axis or plane. Yet in some embodiments, two or more complementary (e.g. interlocking) component pieces do not have the same geometry, but the component pieces are symmetrical around at least one plane, such as a right plane and/or a central front plane.

The component pieces of the present disclosure may comprise, in certain embodiments, at least one planar and/or substantially planar side wall, such as a vertical side wall. In other embodiments, a component piece of a composite implant according to the present disclosure may comprise at least one side wall having an overhang of about 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.022, 0.024, 0.026, 0.028, 0.030, 0.032, 0.034, 0.036, 0.038, 0.040, 0.042, 0.044, 0.046, 0.048, 0.050, 0.055, 0.060, 0.065, 0.070, 0.075, 0.080, 0.085, 0.090, 0.095, 0.100, 0.110, 0.120, 0.130, 0.140, 0.150, 0.160, 0.170, 0.180, 0.190, 0.200, 0.220, 0.240, 0.260, 0.280, 0.300, 0.320, 0.340, 0.360, 0.380, 0.400, 0.420, 0.440, 0.460, 0.480, 0.500, 0.550, 0.600, 0.650, 0.700, 0.750, 0.800, 0.850, 0.900, 0.950, 1.000, 1.100, 1.200, 1.300, 1.400, 1.500, 1.600, 1.700, 1.800, 1.900, and/or 2.000 mm.

In certain embodiments, the overhang is provided in the approximate center of the vertical wall profile.

In certain embodiments, an intersection between a wall of a component piece and a bottom of a component piece, wherein, for example, the bottom of a component piece comprises a flat surface or contoured surface, defines a radius. Moreover, the intersection between a wall and a top surface, such as, for example, a flat or contoured surface, also defines a radius. In an exemplary embodiment, the radius between at least one wall and a bottom surface is less than a radius between a wall and at least one top surface of at least one component piece of a composite implant and/or of a composite implant itself. Furthermore, in an embodiment, a radius between a wall and a bottom surface is equal to a radius between a wall and a top surface. In another embodiment, a radius between a wall and a bottom surface is greater than a radius between a wall and a top surface.

The radius can serve to reduce stress concentration as compared to the case of having a sharp inner corner or a small inner radius. Stress concentration is a standard engineering/applied mechanics concept defined as localized stress higher than the average stress in a component that is typically caused by a sharp inner radius, crack tip, other geometric discontinuity or a mismatch in mechanical properties between one part of a material (such as an inclusion) and the bulk phase. Often cracks can nucleate from stress concentrators and subsequently grow causing a part failure.

In some embodiments, the composite implant has a geometry wherein the vertical sides of the protuberances and recesses of its component pieces are such that there is an interlocking feature whereby the design is the same for each part.

In some embodiments, the geometry on one or both sides of the mating surfaces of two or more component parts comprises a sinusoidal geometry. In some embodiments, the sinusoidal geometry comprises can help promote bony ingrowth when the composite implant is inserted into the body recess of a subject. The mating surface textured will be referred to as having channels and will not be planar or flat. In some embodiments the channels can range in depth of about 0.001, 0.002, 0.003, 0.004, 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.100, 0.110, 0.120, 0.130, 0.140, 0.150, 0.160, 0.170, 0.180, 0.190, 0.200, 0.210, 0.220, 0.230, 0.240, 0.250, 0.260, 0.270, 0.280, 0.290, 0.300, 0.310, 0.320, 0.330, 0.340, 0.350, 0.360, 0.370, 0.380, 0.390, 0.400, 0.410, 0.420, 0.430, 0.440, 0.450, 0.460, 0.470, 0.480, 0.490, 0.500, 0.550, 0.600, 0.650, 0.700, 0.750, 0.800, 0.850, 0.900, 0.950, 1.000, 1.100, 1.200, 1.300, 1.400, 1.500, 1.600, 1.700, 1.800, 1.900, 2.000, 2.100, 2.200, 2.300, 2.400, 2.500, 2.600, 2.700, 2.800, 2.900, 3.000, 3.100, 3.200, 3.300, 3.400, 3.500, 3.600, 3.700, 3.800, 3.900, 4.000, 4.100, 4.200, 4.300, 4.400, 4.500, 4.600, 4.700, 4.800, 4.900, 5.000, 5.500, 6.000, 6.500, 7.000, 7.500, 8.000, 8.500, 9.000, 9.500, and/or 10.000 mm.

The channels can provide for improved host bone ingrowth and micromotion from external cyclic loads on the graft. In some embodiments, the geometry of the channels on one or both sides of the mating surfaces of two or more component parts comprises a circular geometry. In some embodiments, the geometry of the channels on one or both sides of the mating surfaces of two or more component parts comprises an elliptical geometry. In some embodiments, the geometry of the channels on one or both sides of the mating surfaces of two or more component parts comprises a parabolic geometry. In some embodiments, the geometry of the channels on one or both sides of the mating surfaces of two or more component parts comprises a curvilinear geometry, i.e. a cross section of straight lines, curves or a combination of straight lines and curves. In some embodiments, the cross sections of the channels comprise a constant cross section. In some embodiments, the cross sections of the channels comprise varying cross sections throughout the allograft surface onto which they are cut.

Another embodiment of the present invention is a kit, such as a surgical kit. In examples of this kit, the allograft/xenograft, and/or metallic, ceramic, plastic (or other material) implant pieces of the present invention can be provided separately and then assembled at the time of surgery. This would allow for the customization of many different heights and lordosis (degree of angulation between the superior and inferior surfaces) combinations by assembling different combinations of pieces to create the implant of the final size as deemed appropriate by the surgeon for the particular patient's prepared surgical site. For example, manufacturing a 10 mm tall or taller fully CNC machined allograft out of a single piece of bone for anterior cervical discectomy and fusion (ACDF), as shown in FIG. 1, is challenging with the normal anatomical sizes of human femurs and tibias. Making an ACDF cervical allograft of 11 mm or taller from a single piece of bone is almost impossible except for on rare occasion. Utilizing the aforementioned kit, however, making an 11 mm tall ACDF cervical allograft could be accomplished by assembling a net-6 mm bottom piece with a net-5 mm top piece. Likewise, making a 12 mm tall ACDF cervical allograft could be accomplished by assembling a net-6 mm bottom piece with a net-6 mm top piece. The heights of the pieces are referred to as "net-" because they have to be a bit taller to accomplish the net gain in height.

The same scenario with the surgical kit would present itself for lumbar spinal surgery. If for example, during a Transforaminal Posterior Lumbar Interbody Fusion (TLIF) surgical procedure, a surgeon determined that a patient's prepared disc space required a TLIF allograft of 18 mm height with 8 degrees lordosis, that allograft could be assembled intraoperatively with a top piece, net-5 mm tall and 4 degrees lordosis, a middle piece, net-8 mm tall and a bottom piece, net-5 mm tall and 4 degrees lordosis. If the surgeon deemed that the TLIF allograft needed to be 14 mm height with 12 degrees lordosis, that allograft could be assembled intraoperatively with a top piece, net-5 mm tall and 6 degrees lordosis, a middle piece, net-4 mm tall and a bottom piece, net-5 mm tall and 6 degrees lordosis. After assembly the allograft would be ready to be implanted into the subject.

One of ordinary skill in the art will recognize that additional embodiments or implementations are possible without departing from the teachings of the present invention or the scope of the claims which follow. This detailed description, and particularly the specific details of the exemplary embodiments and implementations disclosed herein, is given primarily for clarity of understanding, and no unnecessary limitations are to be understood therefrom, for modifications will become obvious to those skilled in the art upon reading this disclosure and may be made without departing from the spirit or scope of the claimed invention.

The presently-disclosed subject matter further includes any references mentioned therein, which are incorporated herein in its entirety by this reference.

EXPERIMENTAL

This Example demonstrates superior and unexpected properties of the present invention.

Douglas Doud, M. S. E. and Alan Eberhardt, Ph.D. at the University of Alabama at Birmingham, Department of Biomedical Engineering, Musculoskeletal Mechanics Laboratory evaluated one embodiment of the present invention. Specifically, this example uses an embodiment of the present invention comprised of cortical bone allograft. Two types of mechanical tests were performed.

Six assembled cortical allografts were mechanically tested. To mimic insertion into the surgical site and static load-bearing, testing was conducted in two parts—impact testing and compression testing. There were two test groups total, each with a sample size of n=3. The dowels were divided into two test groups: three dowels were impacted first, then retrieved and compressed to failure (specimens CORT1, CORT2 and CORT3); and three dowels were compressed to failure only (specimens CORT4, CORT5 and CORT6).

The first test was to impact the assembled cortical bone allograft into a simulated prepared disc space in the human spine as would be done with the insertion of a structural allograft or device that was to serve as structural interbody support in the spine for spinal fusion.

The second mechanical test was to compress the cortical allografts to failure applying a normal and shear force across the joining feature. Grade 30 polyethylene foam (density=0.48 g/cm$^3$) was utilized as the simulated bone block for the impact surgical insertion simulation testing (Sawbones Block 30 PCF. Pacific Research Laboratories, Inc., Vashon Island, Wash.) conforming to ASTM F-1839 standard (ASTM F1839-08 (2012) Standard Specification for Rigid Polyurethane Foam for Use as a Standard Material for Testing Orthopaedic Devices and Instruments), which describes the material properties of rigid polyethylene foam for use in biomechanical testing. This density was chosen as a model of cancellous bone (Heiner A D, Brown T D, Rossin V, et al. (2001). Frictional Insertion Kinetics of Bone Biopsy Needles. J Biomech Eng 123(6), 629-634. doi:10.1115/1.1407829).

Two separate foam blocks were assembled and held together with aluminum channel held together with C-clamps. A hole was bored between the blocks such that the longitudinal center section of the hole coincided with the mating surfaces of the two blocks.

Three assembled allograft dowels were utilized for this test, CORT1, CORT2 and CORT3. The assembled allograft dowel was placed on the surgical inserter, and advanced into the hole by striking the top of the inserter with an instrumented hammer (Model 086D05 Modally Tuned® Impulse Hammer, PCB Piezotronics, Inc., Depew, N.Y.) being used to strike the inserter. The hammer has a piezoelectric sensor to measure force during impact from 0 to 22,250 Newtons. Equipped with an extender mass and super-soft tip, this hammer has a mass of 0.56 kg, which is comparable to surgical mallets utilized to drive in structural interbody support into prepared disc spaces for spinal surgery. The force of each impact was digitally captured. Once the allograft was seated, the force of the hammer strike was noted. The surgeon continued to strike the surgical inserter until the effort seemed to be substantially greater than the effort exerted while inserting the allograft into cadavers during a previous study. On one cortical dowel, the operator repeatedly attempted to strike the dowel with enough force to break it.

These data are presented in Table 1, below. Average force of impact needed to seat cortical dowels in the urethane foam was 1932 Newtons. No visible damage was noted to the assembled cortical allografts.

TABLE 1

The number of impacts and load data required to seat the allograft into the urethane foam. No visible damage was noted to the three assembled cortical allografts.

| Trial # | # of impacts | Mean (N) | Std. Dev. (N) | Median (N) | Max (N) | Seated at (N) |
|---|---|---|---|---|---|---|
| CORT 1 | 23 | 1428 | 558 | 1286 | 2495 | 1616 |
| CORT 2 | 37 | 1848 | 588 | 1943 | 2928 | 2144 |
| CORT 3 | 50 | 1910 | 805 | 2018 | 3573 | 2036 |
| All CORT | 37 | 1788 | 710 | 1844 | 3573 | 1932 |

Next, the assembled cortical allografts were compressed on an MTS 858 Mini-Bionix mechanical testing system (MTS Systems Corporation, Eden Prairie, Minn.) with aluminum platens that were specifically made to mate with the allografts. The samples were oriented such that the mating sections were rotated 60 degrees from the vertical plane as shown in FIGS. 14 and 15. This resulted in a normal force between the mating sections, $F_N$, and a shear or transverse force, $F_T$, between the mating sections that was one half of the normal force.

Load and displacement were recorded and inflection points in the load-displacement curves were noted as changes in the slope of the curve. Table 2, below shows the compression data.

The first inflection point occurred at an average displacement of 0.51 mm (range 0.34-0.67 mm) at a mean load of 2160 N (range 1576-3370 N). The second inflection point occurred at an average displacement of 1.09 mm (range 0.80-1.43 mm) at a mean load of 3589 N (range 3032-4638 N). The maximum load attained ranged from 4638-7500 N where 7500 N was the maximum load capacity of the load frame (i.e. the specimens had not failed when 7500 N was attained). Four of the six samples were able to withstand 7500 N load across the assembled cortical allograft including one from the group that was impacted prior to compressive testing.

The stiffness was calculated from the test initiation to the first inflection point (Stiffness 1), between first inflection point and the second inflection point (Stiffness 2), and between second inflection point and the maximum load (Stiffness 3). The Stiffness 1 values ranged from 2800-6700 N/mm with a mean value of 5460 N/mm. The Stiffness 2 values ranged from 1730-5120 N/mm with a mean value of 3125 N/mm and the Stiffness 3 values ranged from 3590-6530 N/mm with a mean value of 4935 N/mm.

TABLE 2

Compression data generated from the destructive compressive test as shown in FIGS. 14 and 15. Specimens CORT1, CORT2 and CORT3 were impacted first, then retrieved and compressed to failure and specimens CORT4, CORT5 and CORT6 were compressed to failure only.

|  | Inflection point 1 | | Inflection point 2 | | | | | |
| --- | --- | --- | --- | --- | --- | --- | --- | --- |
|  | Disp. (mm) | Load (N) | Disp. (mm) | Load (N) | Max. load (N) | Stiffness 1 (N/mm) | Stiffness 2 (N/mm) | Stiffness 3 (N/mm) |
| CORT1 | 0.42 | 1945 | 1.43 | 4045 | 6790 | 5460 | 2180 | 5420 |
| CORT2 | 0.67 | 1935 | 1.25 | 4638 | 4638 | 2800 | 5120 | — |
| CORT3 | 0.34 | 1576 | 1.08 | 3108 | 7500 | 5700 | 2720 | 3590 |
| CORT4 | 0.66 | 2180 | 0.88 | 3120 | 7500 | 5460 | 2780 | 6530 |
| CORT5 | 0.34 | 1955 | 0.80 | 3032 | 7500 | 6640 | 1730 | 4200 |
| CORT6 | 0.60 | 3370 | — | — | 7500 | 6700 | 4220 | — |
| Average | 0.51 | 2160 | 1.09 | 3589 | 6905 | 5460 | 3125 | 4935 |

These data show that this allograft joining system is robust enough to withstand the rigors of surgical implantation and the immediate post-operative mechanical environment within human functional spinal units.

REFERENCES

Throughout this document, various references are mentioned. All such references, including those listed below, are incorporated herein by reference.
1. Smith G W. Robinson R A. The treatment of certain cervical-spine disorders by anterior removal of the intervertebral disc and interbody fusion. Journal of Bone and Joint Surgery American. 1958 June; 40-A(3):607-24.

INCORPORATION BY REFERENCE

All publications, patents, and patent applications mentioned in this specification are herein incorporated by reference to the same extent as if each individual publication, patent, or patent application was specifically and individually indicated to be incorporated by reference.

It will be understood that various details of the presently disclosed subject matter can be changed without departing from the scope of the subject matter disclosed herein. Furthermore, the foregoing description is for the purpose of illustration only, and not for the purpose of limitation.

I claim:
1. An implant, comprising:
a body comprising at least a top piece and a bottom piece that have mating interlocking surfaces that couple the pieces together as one piece, the body comprising a front side, back side, top side, bottom side, anterior side, posterior side, and a length extending from the anterior side to the posterior side;
the top piece and the bottom piece each having a superior/upper surface and an inferior/lower surface, wherein at least a portion of the inferior surface of the top piece engages with the superior surface of the bottom piece when the top piece and the bottom piece are coupled together;
the top piece and the bottom piece each comprising at least two protuberances and recesses that are complimentary to the protuberances from a second piece such that the protuberances can be received by the recesses;
said protuberances comprising radii along its height and said recesses comprising radii along its depth;
wherein at least part of the top piece inferior surface and at least part of the bottom piece superior surface comprises ridges that form channels across the respective surfaces, the channels providing intermittent distances between the respective surfaces.

2. The implant of claim 1, wherein at least one of the superior surface of the top piece and the inferior surface of the bottom piece comprise ridges.

3. The implant of claim 1, wherein the superior surface of the top piece and inferior surface of the bottom piece are rounded to form a dowel-shaped implant.

4. The implant of claim 1, wherein the top piece and the bottom piece, when engaging one another, form a common hollow interior space that is generally perpendicular to the inferior and superior surfaces.

5. The implant of claim 4, wherein the common interior space is adapted to receive at least one of osteoconductive material, osteoinductive material, osteogenic material, a pharmaceutical, osteobiologic material and any combination thereof.

6. The implant of claim 4, wherein a protuberance partially borders said common hollow interior space.

7. The implant of claim 1, wherein the common edge of a side and an end are chamfered.

8. The implant of claim 1, wherein at least one protuberance and corresponding recess is concave, biconcave, planoconcave, convex, biconvex, or plano-convex.

9. The implant of claim 1, wherein at least one protuberance spans from the front surface of a piece to the back surface of a piece.

10. The implant of claim 1, wherein a protuberance and corresponding recess is round or partially rounded.

11. The implant of claim 1, wherein a protuberance and corresponding recess is circular or partially circular, sinusoidal or partially sinusoidal, parabolic or partially parabolic, elliptical or partially elliptical.

12. The implant of claim 1, wherein the top piece inferior surface comprises an upper machined surface and a lower machined surface defined by the height of the protuberances; and the bottom piece superior surface comprises an upper machined surface and a lower machined surface defined by the sides (vertical walls) of the protuberances.

13. The implant of claim 12, wherein the upper machined surfaces of the top and bottom pieces comprise channels.

14. The implant of claim 13, wherein the lower machined surfaces of the top and bottom pieces are substantially flat.

15. The implant of claim 13, wherein the channels provide intermittent distances between the inferior and superior surfaces.

16. The implant of claim 1, wherein the top and bottom pieces comprise allograft bone tissue.

17. The implant of claim 1, wherein the top and bottom pieces comprise cortical bone tissue.

18. The implant of claim 1, wherein the top and bottom pieces comprise xenograft material, autograft material, and combinations thereof.

19. The implant of claim 1, wherein the top and bottom pieces comprise at least one of cortical bone, cancellous bone, titanium, carbon fiber, tantalum, stainless steel, cobalt chromium, polyetheretherketone (PEEK) polymer, and any combination thereof.

20. The implant of claim 19, wherein the cortical bone is partially or fully demineralized.

21. The implant of claim 19, wherein the cancellous bone is partially or fully demineralized.

22. The implant of claim 1, wherein the first protuberance is a different shape than the second protuberance.

23. The implant of claim 1, further comprising a second top piece that has a superior surface with protuberances and recesses that correspond with the inferior surface of the first top piece, and has an inferior surface with protuberances and recesses that correspond with the superior surface of the bottom piece.

24. The implant of claim 23, wherein the second top piece comprises recesses on the superior and inferior surfaces to intermittently engage the adjacent surfaces of the first top piece and the bottom piece.

25. The implant of claim 23, wherein the first top piece inferior surface comprises an upper machined surface and a lower machined surface defined by the height of the protuberances; the second top piece comprises an upper machined surface and a lower machined surface defined by the height of the protuberances; and the bottom piece superior surface comprises an upper machined surface and a lower machined surface defined by the height of the protuberances; and wherein the protuberances comprise ridges, the lower machined surfaces are substantially flat, and the ridges intermittently engage the lower machined surfaces.

26. The implant of claim 23, wherein the superior surface of the first top piece and the inferior surface of the bottom piece are rounded to form a dowel-shaped implant.

27. The implant of claim 26, wherein the superior surface of the first top piece and the inferior surface of the bottom piece comprises ridges.

28. The implant of claim 1, the top piece being in combination with the bottom piece but not engaged.

29. The implant of claim 1, wherein the top piece and the bottom piece are engaged.

30. A kit that comprises at least one top piece and at least one bottom piece of claim 1.

31. The implant of claim 1, wherein the recess and protuberance have a vertical wall that has an overhang in the approximate center of the wall.

32. The implant of claim 31, wherein the vertical wall has an inner radius and an outer radius that may be the same radii, the inner radius may be greater than the outer radius or the inner radius may be less than the outer radius.

33. An implant, comprising:
a body comprising at least a first top piece, at least one second top piece/ middle piece, and a bottom piece that have mating interlocking surfaces that couple the pieces together as one piece, the body comprising a front side, back side, top side, bottom side, anterior side, posterior side, and a length extending from the anterior side to the posterior side;
the first top piece, second top piece, and the bottom piece each having a superior/upper surface and an inferior/lower surface, wherein at least a portion of the inferior surface of the top piece engages with a portion of the superior surface of the second top piece, and at least a portion of the inferior portion of one of the at least one second top piece engages with at least a portion of the superior surface of the bottom piece when pieces are coupled together;
the top piece comprising at least two recesses;
the second top piece comprising at least two protuberances on the superior surface that correspond with and are received by complimentary recesses of the top piece when engaged with the top piece, and at least two protuberances on the inferior surface;
the bottom piece comprising at least two corresponding recesses that are complimentary to and receive the protuberances from a second top piece when engaged;
said protuberances comprising radii along its height and said recesses comprising radii along its depth;
wherein at least part of the surfaces comprising protuberances comprise ridges that form channels across the respective surfaces, the channels providing intermittent distances between the respective surfaces when engaged.

* * * * *